(12) United States Patent
Koyama et al.

(10) Patent No.: US 11,065,008 B2
(45) Date of Patent: Jul. 20, 2021

(54) EMBOLIC COIL

(71) Applicants: SHINSHU UNIVERSITY, Matsumoto (JP); Mikuro Spring Co., Ltd., Suwa (JP)

(72) Inventors: Junichi Koyama, Matsumoto (JP); Takuya Kojima, Suwa (JP); Makoto Natori, Suwa (JP); Yusuke Sato, Suwa (JP)

(73) Assignees: SHINSHU UNIVERSITY, Matsumoto (JP); Mikuro Spring Co., Ltd., Suwa (JP)

( * ) Notice: Subject to any disclaimer, the term of this patent is extended or adjusted under 35 U.S.C. 154(b) by 124 days.

(21) Appl. No.: 16/303,020

(22) PCT Filed: Dec. 6, 2016

(86) PCT No.: PCT/JP2016/086159
§ 371 (c)(1),
(2) Date: Nov. 19, 2018

(87) PCT Pub. No.: WO2017/208483
PCT Pub. Date: Dec. 7, 2017

(65) Prior Publication Data
US 2019/0142436 A1    May 16, 2019

(30) Foreign Application Priority Data

May 31, 2016 (JP) .............................. JP2016-109073

(51) Int. Cl.
*A61B 17/12* (2006.01)

(52) U.S. Cl.
CPC .. *A61B 17/12145* (2013.01); *A61B 17/12113* (2013.01); *A61B 17/12163* (2013.01); *A61B 2017/1205* (2013.01)

(58) Field of Classification Search
CPC ........ A61B 17/12113; A61B 17/12145; A61B 17/12163; A61B 2017/1205; A61B 17/12;
(Continued)

(56) References Cited

U.S. PATENT DOCUMENTS 8,690,907 B1 * 4/2014 Janardhan ........ A61B 17/12109
606/200
9,011,480 B2 * 4/2015 Divino ............. A61B 17/12031
606/200
(Continued)

FOREIGN PATENT DOCUMENTS

JP         4961349 B      6/2012
JP         2015-511828 A  4/2015

OTHER PUBLICATIONS

Extended European Search Report dated Oct. 23, 2019 for the corresponding European Patent Application No. 16904107.6.
(Continued)

*Primary Examiner* — Erich G. Herbermann
(74) *Attorney, Agent, or Firm* — Leason Ellis LLP

(57) ABSTRACT

An embolic coil is formed by being spirally wound by an element wire and is filled into an aneurysm. The embolic coil includes: a first coil portion, in which a large-diameter coil portion wound to have a large diameter D1 and a small-diameter coil portion wound to have a diameter D2 smaller than the large-diameter coil portion are arranged in a plurality of coils and alternately in a longitudinal direction Y of the embolic coil. A second coil portion is wound to be continuous with the first coil portion and to have a surface flatter than the first coil portion.

9 Claims, 18 Drawing Sheets

(58) Field of Classification Search
CPC ........ A61B 17/12031; A61B 17/12036; A61B 17/12022; A61B 17/12122; A61B 17/12172
See application file for complete search history.

(56) References Cited

U.S. PATENT DOCUMENTS

| | | |
|---|---|---|
| 2006/0116711 A1 | 6/2006 | Elliott et al. |
| 2010/0010533 A1 | 1/2010 | Burke et al. |
| 2013/0190801 A1 | 7/2013 | Divino et al. |
| 2015/0257765 A1 | 9/2015 | Barkenbs et al. |

OTHER PUBLICATIONS

International Search Report dated Feb. 28, 2017 for the corresponding PCT International Application No. PCT/JP2016/086159.

\* cited by examiner

EMBOLIC COIL

CROSS-REFERENCE TO RELATED PATENT APPLICATIONS

This application is a U.S. National Phase Application under 35 U.S.C. § 371 of International Patent Application No. PCT/JP2016/086159, filed Dec. 6, 2016, and claims the benefit of Japanese Patent Application No. 2016-1090, filed on May 31, 2016, all of which are incorporated herein by reference in their entirety herein. The International Application was published in Japanese on Dec. 7, 2017 as International Publication No. WO/2017/208483 under PCT Article 21(2).

FIELD OF THE INVENTION

The present invention relates to an embolic coil filled into an aneurysm as a method for treating aneurysms.

BACKGROUND OF THE INVENTION

There are various conventional treatment methods for aneurysms. The various treatment methods include a method, with the objective of preventing the aneurysm from rupturing, by guiding and filling an embolic coil into the aneurysm via a catheter to prevent blood flowing in the blood vessels from entering inside the aneurysm to proactively form a thrombus or clot that blocks the flow of blood into the aneurysm. Typical examples of the embolic coil in the aforementioned treatment method include a method described in Japanese Patent No. 4961349 and the like.

Japanese Patent No. 4961349 discloses an embolic coil having a convex-concave structure on its surface, in which a large-diameter coil portion wound by wire to form a large diameter and a small-diameter coil portion wound by wire to form a small diameter coil portion are provided, and large-diameter coil portions and a small-diameter coil portions alternate along the entire length of the embolic coil.

Problems to be Solved by Invention

The filling of an embolic coil into an aneurysm is usually performed as described next. Namely, an embolic coil is pushed out from the distal end of a catheter and guided into the aneurysm, and the initially guided portion curves into a ring shape along the inner surface of the aneurysm, and the guided embolic coil gradually creates a plurality of ring shape portions that form a frame. The subsequent embolic coil is sequentially filled into this region enclosed by the frame.

The conventional embolic coil of the related art described in Japanese Patent No. 4961349 has a convex-concave structure in which a large-diameter coil portion and the small-diameter coil portion are alternately present in the entire longitudinal direction.

When the embolic coil is guided into the aneurysm to form the frame, the ring-like portion gradually increases in the aneurysm along with progress of the frame formation, but due to the convex-concave structure, the large diameter coil portion tends to become easily caught or hang up, which makes smoothly forming the frame in the aneurysm difficult. However, the above-mentioned description of Japanese Patent No. 4961349, gives no consideration whatsoever to the problem that the large-diameter coil portion becomes easily caught.

When catching of the large diameter coil portion occurs, the embolic coil, extruding into the aneurysm from the distal end of the catheter, is partially withdrawn into the catheter. After the large diameter coil portion no longer catches, the embolic coil is pushed out again. The greater the number of times that the embolic coil is "withdrawn and again pushed forward", the longer the time needed to fill into the embolic coil, resulting in the problem of poor operability.

Also in a state where the frame has formed to a certain extent, a portion where the large diameter coil portion is caught due to the presence of the convex-concave structure is formed at the mutual contact positions (or intersecting positions) between the ring-shaped portions, and the size and shape of the frame are generally fixed so that a frame is stabilized.

<Expansion and Deformation of Aneurysm Volume>

However, as the embolic coil is guided further inwards, the aneurysm might expand and deform to a larger size than at the start of guidance into the aneurysm. The frame however has a fixed size and shape and so cannot follow up on the expansion and deformation of the volume of the aneurysm. And the area of the void between the outer side of the aneurysm and the inner surface of the aneurysm becomes large. When this void region becomes large, the problem arises that the position of the frame in the aneurysm becomes unstable.

An object of the present invention is to provide such an embolic coil as to be capable of smoothly forming a frame when forming a frame in an aneurysm by an embolic coil and also capable of following up on the expansion and deformation of the volume of the aneurysm.

SUMMARY OF THE INVENTION

Means for Solving Problems

An embolic coil according to the first embodiment of the present invention to solve the above problems is formed by being spirally wound by wire and is filled into an aneurysm, and characterized by including: a first coil portion, in which a plurality of large-diameter coil portions wound to have large diameter and small-diameter coil portions wound to have a diameter smaller than that of the large-diameter coil portions, are alternately present in a longitudinal direction of the embolic coil; and a second coil portion, which is continuous with the first coil portion and wound to have a flatter surface than the first coil portion.

Here, the "large diameter" of the large diameter coil portion may be uniform over the entire length in the axial direction (longitudinal direction of the embolic coil) of the large diameter coil portion, but preferably has a structure such that the portion of the coil with a maximum outer diameter is provided in the center and the dimensions of coils are reduced gradually and symmetrically in the axial direction. The "flat surface" in the "second coil portion wound to have a surface flatter than the first coil portion" means not only that the second coil portion is wound with a uniform diameter and with the same diameter over the entire length, but also that the diameter may be reduced (sloped) from one end side to the other end side. This signifies that the diameter need not be uniform over the entire length, and it is acceptable as long as the surface of the second coil portion is smooth.

Furthermore, the ratio of presence of the first coil portion and the second coil portion is appropriately set and used to match the size and shape of the aneurysm.

In an early stage of guiding the embolic coil into the aneurysm, an outer shell structure for the embolic coil called a frame is formed in the aneurysm. The frame is generally formed by way of the following forming mechanism. When the embolic coil is guided into the aneurysm, the embolic coil is curved into a ring shape and is filled in the aneurysm.

A plurality of ring-shaped embolic coil portions are formed three-dimensionally at this time in the aneurysm and are positioned along the inner surface in the aneurysm. The plurality of ring-shaped portions positioned along the inner surface of the aneurysm allows smoothly guiding the subsequent embolic coil and forms a basic outer shell structure, called a "frame", that determines the filling configuration of the final embolic coil. A force to expand the frame outwards is generated by the repulsive force (elastic force) of the curved embolic coil, and the ring-shaped portion is positioned and held along the inner surface of the aneurysm by way of this force.

In this aspect the embolic coil includes both of: the first coil portion having a convex-concave structure on the surface due to a structure whereby a plurality of the large-diameter coil portions and the small-diameter coil portions are alternately provided; and the second coil portion in the flat surface cylindrical structure, which is wound to form a flat surface.

According to this aspect, when the embolic coil is guided into the aneurysm and several ring-shaped portions, in a curved state in a ring shape in the aneurysm are produced to form the frame, even if the amount of the ring-shaped portion increases along with progress in the formation of the frame, the possibility of the large-diameter coil portion catching is reduced due to the presence of the flat cylindrical structure portion. Therefore, the frame can be smoothly formed without being bothered by the catching of the large-diameter coil portion.

Further, in the frame, at the stage that the frame is formed, at a contact position (intersecting position) between mutual ring-shaped portions, the position where the large-diameter coil portion is caught is created due to the presence of the convex-concave structure. As a result, an anchor effect is produced due to the catching of the large-diameter coil portion, and thereby the structure of the frame or namely the three-dimensional structure formed with the plurality of ring-shaped portions is stabilized.

<Expansion and Deformation of Aneurysm Volume>

As the embolic coil is guided further inwards while the large diameter coil portion is caught, the volume of the aneurysm expands as the guiding of the embolic coil progresses, compared to when first starting to guide the coil. In other words, the volume of the aneurysm expands and deforms. According to this aspect, since the flat cylindrical structure portion (second coil portion) is in the portion forming the frame structure, when the volume of the aneurysm expands and deforms, the position where the large diameter coil portion is caught can be moved along the cylindrical structure portion.

Here, the cylindrical structure (second coil portion) portion of the embolic coil provides a larger repulsive force toward the curve and deformation than the convex-concave structure (first coil portion) portion. Due to the repulsive force of the cylindrical structure portion, the force that expands the frame outwardly is stronger than conventional embolic coils which only have a convex-concave structure. The repulsive force also causes the position where the large diameter coil portion is caught to move in the direction for expanding the frame along the cylindrical structure portion. In other words, the frame can become larger to match the expansion and deformation of the aneurysm volume.

The possibility that the position of the frame will become unstable in the expanded and deformed aneurysm is in this way reduced. The ring-shaped portion is therefore positioned along the inner surface of the enlarged and deformed aneurysm, and the frame can be held firmly in the aneurysm.

In addition, according to this aspect, since the frame is formed while being held firmly within the aneurysm as described above, when the subsequent embolic coil is further filled into the aneurysm, the possibility of the frame going out of the aneurysm can be reduced.

Also in this aspect, by configuring the part of the embolic coil to be fed into the frame, after the frame is formed, by using the second coil portion in the cylindrical structure, the subsequent embolic coil can be smoothly and continuously fed into the frame without catching since the portion being fed into the frame has the cylindrical structure (second coil portion) as described above.

<Irregularly Shaped Aneurysm>

Aneurysms sometimes have an irregular shape with one or more portions whose inner surface shape is not uniform but partially recessed.

According to the present aspect, when the frame is formed, due to the presence of the cylindrical structure (second coil portion), the second coil portion in the cylindrical structure can protrude, with little resistance, from the inside of the frame to the outside, through the clearance of the ring-shaped portion forming the ring. In this way, even if the shape of the aneurysm is irregular and a void region is likely to form between the outer side of the frame and the inner surface of the aneurysm, the second coil portion can easily enter into the void region. The embolic coil of this aspect can therefore cope not only with well-shaped aneurysms but also with irregularly shaped aneurysms, and can form a frame that can easily cope with the irregularly shaped aneurysm.

An embolic coil according to a second aspect of the present invention is based on the embolic coil according to the first aspect, and characterized in that the outer diameter of the second coil portion is the same size as the maximum outer diameter of the large diameter coil portion.

Here, "the same" in "the same as the maximum outer diameter" in this specification is used in a broad sense meaning that it does not have to be exactly the same. In other words, the term "the same" is used within a wider scope that allows some differences in the outer diameter as long as the rectilinearity of the embolic coil is substantially obtained when the embolic coil is fed into the catheter described later.

According to this aspect, since the outer diameter of the second coil portion is the same as the maximum outer diameter of the large diameter coil portion of the first coil portion when passing the embolic coil through the catheter to the site where the aneurysm occurs, both of the first coil portion and the second coil portion can likewise be advanced while guided by the inner surface of the catheter. Thereby, the embolic coil can move stably with good rectilinearity and reach the aneurysm site.

An embolic coil according to a third aspect of the present invention is based on the embolic coil according to the first aspect or the second aspect, characterized in that the first coil portion having a predetermined length is positioned at the distal end of the embolic coil.

Here, the "predetermined length" in "the first coil portion having a predetermined length" should preferably be set to match the length needed for forming the frame in consideration of the difference in the size and shape of the aneurysm.

According to this aspect, since the first coil portion having a predetermined length is positioned at the distal end of the embolic coil, the convex-concave structure (first coil portion) is first guided into the aneurysm. So the formation of the frame can start in a state where there is less catching of the large diameter coil portion.

In the aneurysm, in a state where the distal end portion of the embolic coil forms the frame, the large diameter coil portion can become caught on the convex-concave structure. The stability of the position of the distal end portion of the embolic coil within the frame structure can therefore be improved.

An embolic coil according to a fourth aspect of the present invention is based on the embolic coil according to any one of the first aspect to the third aspect, and characterized in that the first coil portion having a predetermined length and the second coil portion having a predetermined length are repeatedly provided in the longitudinal direction.

Here, the "predetermined length" in the first coil portion and the second coil portion is not limited to the repetition at the same length, in terms of repetition in the longitudinal direction. In other words, a structure may be employed that repeatedly provides the first coil portions each having different lengths and the second coil portions each having different lengths.

Further, the "predetermined length" in "the second coil portion having the predetermined length" may be longer than, shorter than, or the same as the predetermined length of the first coil portion, or may be combination of two or more thereof.

According to this aspect, since the convex-concave structure portion (first coil portion) and the cylindrical structure portion (second coil portion) are repeatedly provided in the longitudinal direction of the embolic coil, the repeatedly provided cylindrical structure portions allow smoother frame formation with much less catching of the large diameter coil portion, when the frame is formed by the embolic coil in the aneurysm.

Further, the cylindrical structure portions repeatedly provided in the constituent portion of the frame structure create a state in which portions having a large repulsive force toward the curve and deformation are repeatedly provided in the constituent portion of the frame structure. Accordingly, the embolic coil can more effectively follow-up on and become larger along with the expansion and deformation of the aneurysm volume.

The embolic coil according to a fifth aspect of the present invention is based on the embolic coil according to the third aspect, and characterized in that the portion of the distal end of the embolic coil continuing to the first coil portion is provided with the second coil portion having a length longer than the first coil portion.

Here, the term "longer" in "the second coil portion having a length longer than the first coil portion" in this specification is used to cover a broad range signifying from a second coil portion just a little bit longer than the first coil portion to a second coil portion several times longer than the first coil portion. Furthermore, the term is meant to include an embolic coil, in which the first coil portion is present only at the distal end portion of the embolic coil and the remaining portions are all constituted with the second coil portion.

According to this aspect, after formation of the frame starts in a state where the large-diameter coil portion is not significantly caught in the aneurysm, the cylindrical elongated second coil portion can be smoothly fed into the aneurysm. Even when the aneurysm is highly irregularly shaped and the void region is likely to form between the outer side of the frame and the inner surface of the aneurysm, the embolic coil can be filled into the void region because the second coil portion is long. Namely, the embolic coil can satisfactorily be filled not only into well-shaped aneurysms but also into highly irregularly shaped aneurysms.

An embolic coil according to a sixth aspect of the present invention is based on the embolic coil according to any one of the first aspect through the fifth aspect, and characterized in that the large diameter coil portion is wound such that an outer surface forms a spherical convex curved surface.

According to this aspect, since the large diameter coil portion is wound so that the outer surface thereof forms a spherical convex curved surface, the embolic coil is moved smoothly within the catheter. In the step for forming the frame constituted by a plurality of ring-shaped portions after the embolic coil is fed into the aneurysm from the catheter, even if the embolic coil has a convex-concave structure portion, guiding of the embolic coil can proceed with less catching between separate parts of the embolic coil, until a frame having a ring-shaped portion corresponding to the size and shape of the aneurysm is formed. After the frame is formed to a certain extent, the separate parts of the embolic coil are caught by one another due to a locking function by the convex-concave structure (first coil portion) at each contact position of each ring-shaped portion forming the frame.

Namely, in the stage (dynamic state) in the course of forming the frame, the large diameter coil portion forms a spherical convex curved surface on the outer surface thereof, so that one large diameter coil portion is less likely to caught by other large diameter coil portions or small diameter coil portions. And in the stage (static state) after frame forming is complete, one large diameter coil portion is caught by other large diameter coil portions or small diameter coil portions, so that the frame is efficiently formed in a stable state.

An embolic coil according to a seventh aspect of the present invention is based on the embolic coil according to any one of the first aspect through the sixth aspect, and is characterized in that the small diameter coil portion is wound such that an outer surface forms a spherical concave curved surface.

According to this aspect, when the first coil portion enters into the aneurysm and is curved, since the outer surface of the small-diameter coil portion is wound to form a spherical concave curved surface, the first coil portion can be curved with less resistance compared to the small-diameter coil portion that is wound to have a cylindrical shape with a uniform diameter.

In addition, the filling of the subsequent embolic coil can be performed more smoothly because of the presence of the concave curved surface since the possibility of catching of the large diameter coil portion is reduced.

An embolic coil according to an eighth aspect of the present invention is based on the embolic coil according to any one of the first through the seventh aspect, in which a primary shape, in which the first coil portion and the second coil portion are formed, is formed relative to the wire, and a secondary shape used for forming a frame is formed relative to a predetermined length portion of the distal end of the embolic coil.

According to this aspect, since the secondary shape for forming the frame is formed relative to the predetermined length portion of the distal end of the embolic coil, due to the effect of forming the secondary shape, the embolic coil that moves in the catheter in the primary shape state, is automatically transformed into the secondary shape at the stage where the embolic enters into the aneurysm from the distal end of the catheter. In other words, the predetermined length portion of the distal end of the embolic coil is smoothly transformed into the ring-shaped frame along the inner surface of the aneurysm. At the contact position (intersecting position) between the ring-shaped portions forming the frame formed by the secondary shape, portions where different portions of the embolic coil are caught on one other due to the convex-concave structure of the first coil portion are created, so the frame is stably formed and held.

Further, since the secondary shape is not formed except at the distal end portion of the embolic coil, when the subsequent embolic coil is pushed into the frame formed in this way, the subsequent embolic coil can be guided while being flexibly adapted and curved to suit an inner space that does not have a uniform shape in the frame.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

An embolic coil according to the embodiments of the present invention will hereinafter be described in detail while referring to the accompanying drawings.

In the following description, an overview of catheter treatment using an embolic coil will first be described based on FIG. 1. Next, a specific configuration of the embolic coil according to the first embodiment of the present invention will be described based on FIG. 2 and FIG. 3 and thereafter based on FIG. 4 and FIG. 5, the process for guiding an embolic coil into an aneurysm by using the embolic coil will be described.

Next, a case where an embolic coil is guided into an irregularly shaped aneurysm will be described based on FIG. 6.

Then, a specific configuration of the embolic coil according to the second embodiment of the present invention will be described based on FIG. 7 and FIG. 8, and thereafter based on FIG. 9 to FIG. 11, the process for guiding an embolic coil into an aneurysm by using the embolic coil will be described.

Next, a case where the embolic coil is guided into an irregularly shaped aneurysm will be described based on FIG. 12 and FIG. 13.

An example of the filling state of the embolic coil after completion of filling, according to the second embodiment, will be described based on FIG. 14. An example of the filling state of the embolic coil after completion of filling, according to the first embodiment, will be described based on FIG. 15.

Further, the configuration of the embolic coil according to the third embodiment, fourth embodiment, and fifth embodiment of the present invention will be described based on FIG. 16 to FIG. 18 while focusing on the difference from the first embodiment. Finally, other embodiments having a different configuration from these embodiments will be mentioned.

First Embodiment (See FIG. 1 to FIG. 6)

Figure 1:
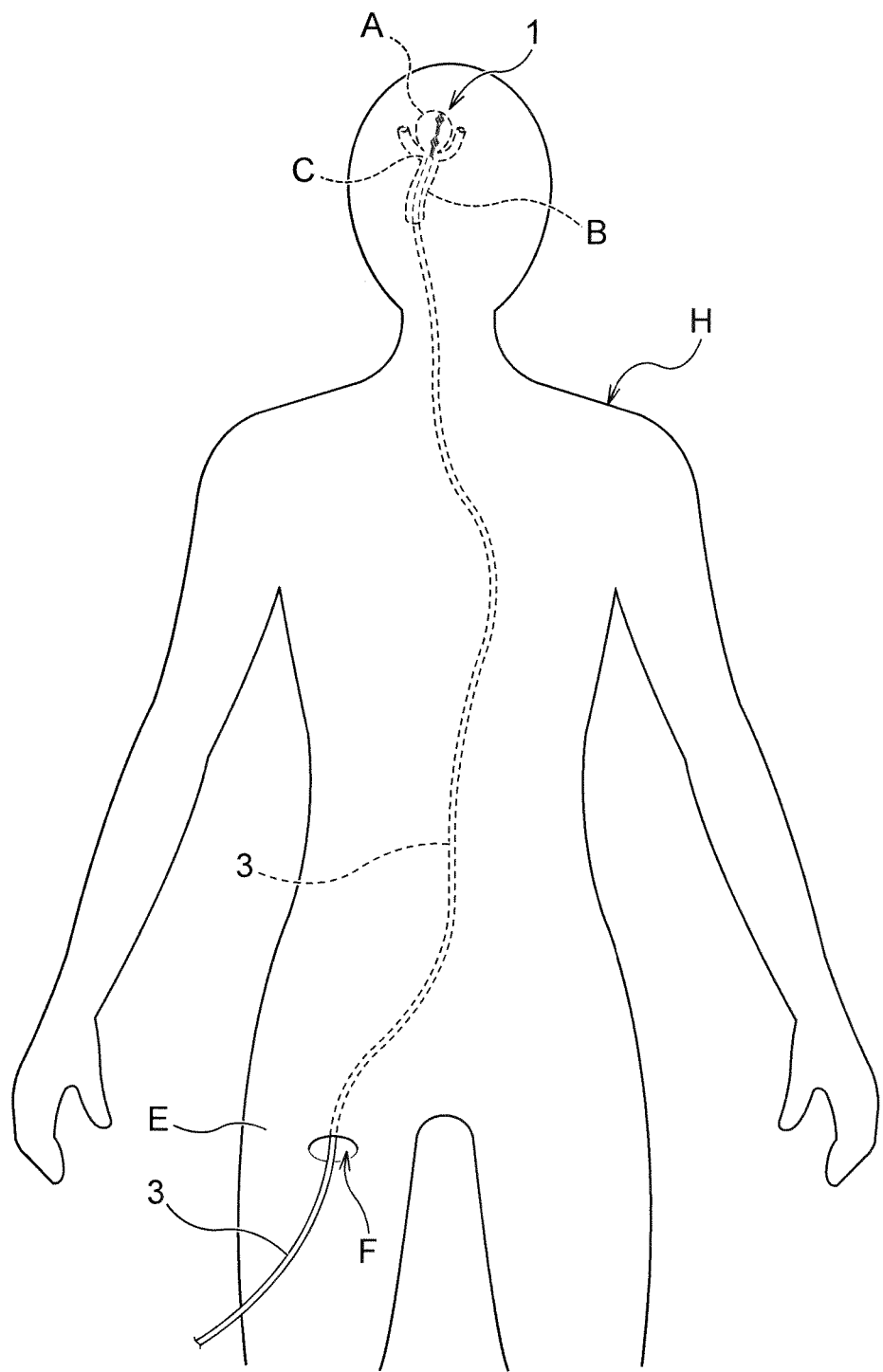
FIG. 1 is an explanatory diagram showing an outline of catheter treatment using an embolic coil.

(1) Outline of Catheter Treatment that Utilizes an Embolic Coil (See FIG. 1)

An embolic coil 1 is used in aneurysm treatment which employs a catheter 3 for the purpose of preventing rupture of an aneurysm A. Specifically, for example, when the aneurysm A develops at a bifurcation C of a cerebral artery B of a human body H, as shown in FIG. 1, an insertion opening F for inserting the catheter 3 into a crotch portion E is created, and the catheter 3 with a diameter of about 2 mm, for example, is inserted from a femoral artery of the crotch portion E.

Further, a contrast agent is injected into a blood vessel, and the catheter 3 is guided to a position slightly deeper inside the aneurysm A at the site where the aneurysm A is developing while observing a fluoroscopic image obtained by X-rays. The embolic coil 1 of the present invention is then inserted into the catheter 3, and guided to a distal end of the catheter 3 along an inner wall of the catheter 3. A distal end portion of the embolic coil 1 is extruded from an opening of the distal end and guided into the aneurysm A. Thereafter, the embolic coil 1 is pushed outwards, and guided and filled into the aneurysm A.

Though the aneurysm sometimes takes other forms such as a saccular aneurysm and a dissecting aneurysm developed in non-bifurcated areas other than the bifurcation C, these types of aneurysms can also be treated with the embolic coil 1.

Figure 2:
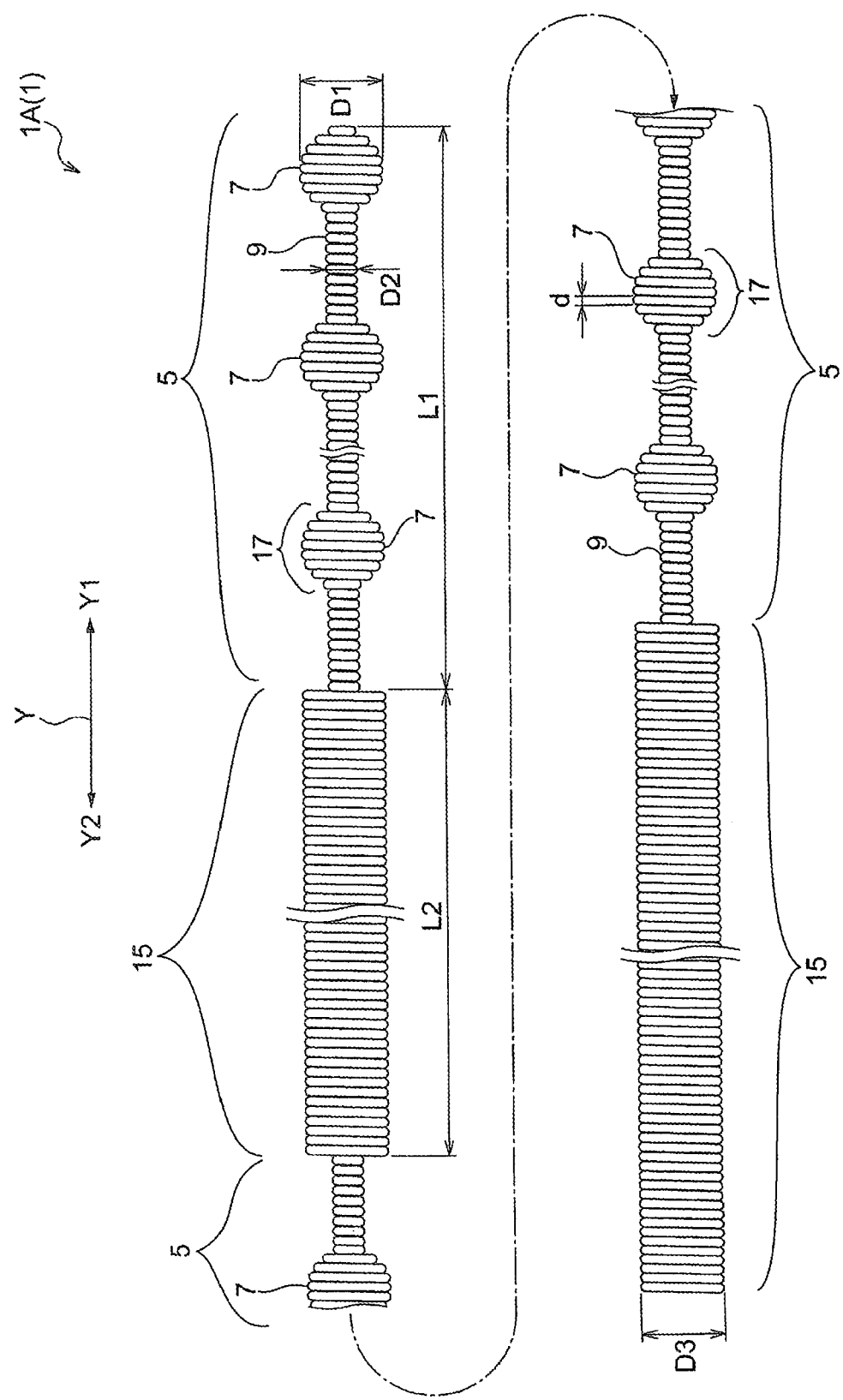
FIG. 2 is a view showing a first embodiment of the present invention, and is a side view showing a primary shape of an embolic coil.
Figure 3:
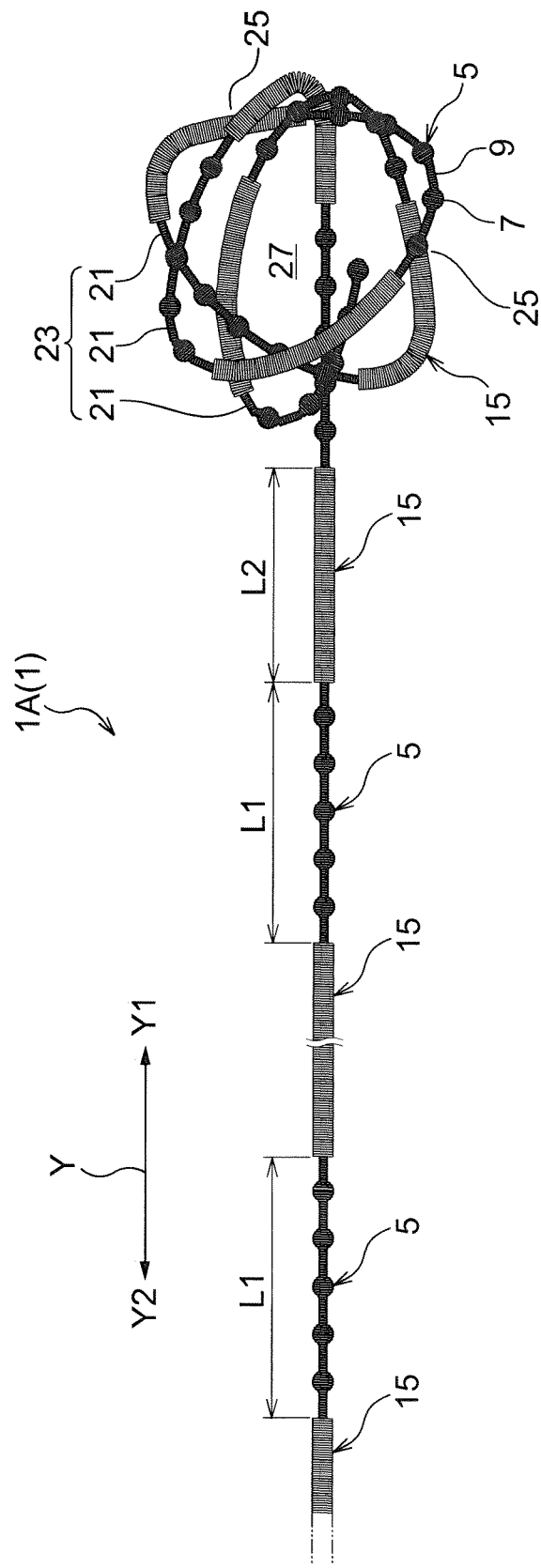
FIG. 3 is a view showing a first embodiment of the present invention, and is a side view showing a secondary shape of an embolic coil.

(2) Specific Configuration of the Embolic Coil (See FIG. 2 and FIG. 3)

The embolic coil 1 of the present embodiment is formed by spirally winding a wire 2 and basically includes: a first coil portion 5, in which a large-diameter coil portion 7 wound to have a maximum outer diameter of D1 and a small-diameter coil portion 9 wound to have a diameter D2 smaller than the large-diameter coil portion 7 are alternately provided in a plurality in the longitudinal direction Y of the embolic coil 1; and a second coil portion 15 wound to be continuous from the first coil portion 5 and to have a surface flatter than the first coil portion 5.

The first coil portion 5 has a convex-concave structure on its surface due to the arrangement of a plurality of the alternately provided large-diameter coil portions 7 and the small-diameter coil portions 9. In the present embodiment, the second coil portion 15 has a cylindrical structure with a flat surface, in which the wire is wound to maintain a uniform diameter D3. Here, the "large diameter" of the large-diameter coil portion 7 may have a width that is uniform along the entire length in the axial direction (longitudinal direction Y of the embolic coil 1) of the large diameter coil portion 7, but preferably as shown in FIG. 2 has a structure, in which the maximum outer diameter portion is provided in the center and the diameter is gradually reduced symmetrically in the axial direction.

The embolic coil 1A according to the present embodiment has a structure in which the first coil portion 5 with a predetermined length L1 and the second coil portion 15 with a predetermined length L2 are repeatedly provided in the longitudinal direction.

The ratio of presence of the first coil portion 5 and the second coil portion 15 is appropriately set relative to the size and shape of the aneurysm, but here as shown in FIG. 3, there are plural sets of the first coil portion 5 and the second coil portion 15 in a frame 23 formed in the aneurysm A. In FIG. 3, the predetermined length L1 of the first coil portion 5 is formed larger than the predetermined length L2 of the second coil portion 15 so that L1>L2, but the present invention is not limited thereto. The relationship between L1 and L2 may be reversed, or L1 and L2 may have the same length.

In the example of the present embodiment shown in FIG. 2, an outer surface of the large diameter coil portion 7 constituting a part of the first coil portion 5 is formed in the shape of spherical convex curved surface 17. The small diameter coil portion 9 constituting another portion of the first coil portion 5 is formed as an example in a cylindrical shape linearly extending in the longitudinal direction Y.

On the other hand, the second coil portion 15 is formed for example with the same outer diameter D3 as the maximum outer diameter D1 of the large-diameter coil portion 7 of the first coil portion 5, and has a cylindrical structure linearly extending in the longitudinal direction Y.

In the structure shown in FIG. 2 and FIG. 3, a connected portion between the second coil portion 15 and the first coil portion 5 continues to the small diameter coil portion 9, so that a step is formed at a boundary portion therebetween by the diameter D2 and the diameter D3. The step can be eliminated by making the connected portion of the second coil portion 15 continue to a portion of the maximum outer diameter D1 of the large diameter coil portion 7.

As a material of the embolic coil 1A configured in this way, a wire (shown as wire 2), having a wire diameter d of 15 μm to 100 μm, preferably 30 μm to 75 μm, and made from platinum, tungsten, or stainless steel can for example be used. Since these materials are resistant to corrosion and combine appropriate rectilinearity and flexibility, when the embolic coil 1A moves inside the catheter 3, the embolic coil 1A moves smoothly while maintaining appropriate rectilinearity, and when the coil 1A is guided into the aneurysm 1A, this flexibility functions to make the coil 1A curve smoothly and fill the aneurysm A.

As the outer diameter D2 of the small-diameter coil portion 9 of the first coil portion 5, 0.06 mm to 0.40 mm, preferably 0.12 mm to 0.30 mm can be adopted. The maximum outer diameter D1 of the first coil portion 5 and the outer diameter D3 of the second coil portion 15 should be larger than the outer diameter D2 of the small diameter coil portion 9 and should allow smooth movement in the catheter 3, and can be set for example, 0.2 mm to 0.5 mm, preferably 0.25 mm to 0.47 mm.

FIG. 2 shows the embolic coil 1A in a primary shape when moving inside the catheter 3. However, as shown in FIG. 3, the embolic coil 1A of a secondary shape having a larger coil diameter (for example, 3 mm to 30 mm) may be formed in advance so that the frame 23 is formed more easily to match the size and shape of the aneurysm A. The formation of the secondary shape may be omitted. The embolic coil 1A of the present embodiment is confirmed as capable of smoothly forming the frame 23 without forming a secondary shape.

Figure 4:
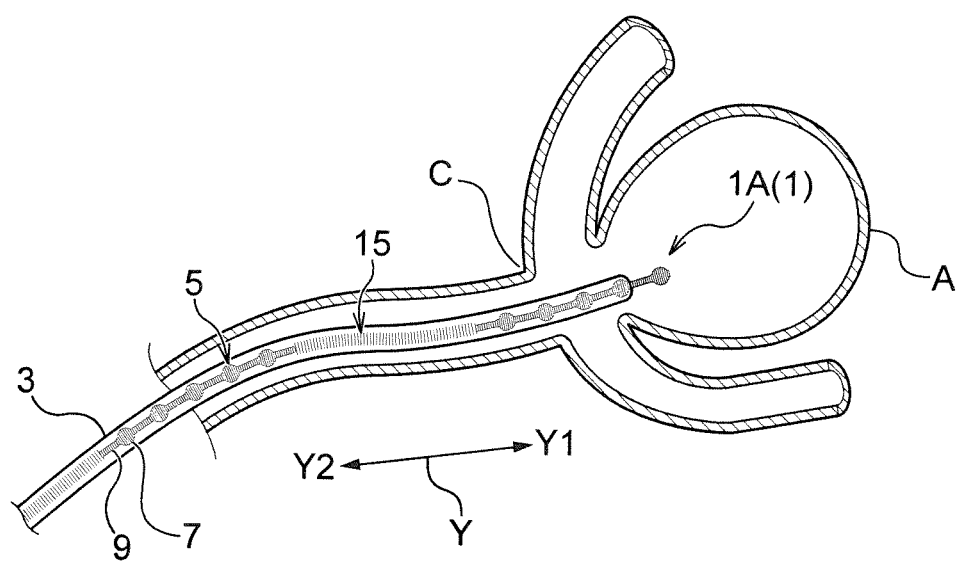
FIG. 4 is a view showing a first embodiment of the present invention, and is an explanatory diagram showing an embolic coil before starting to guide.
Figure 5:
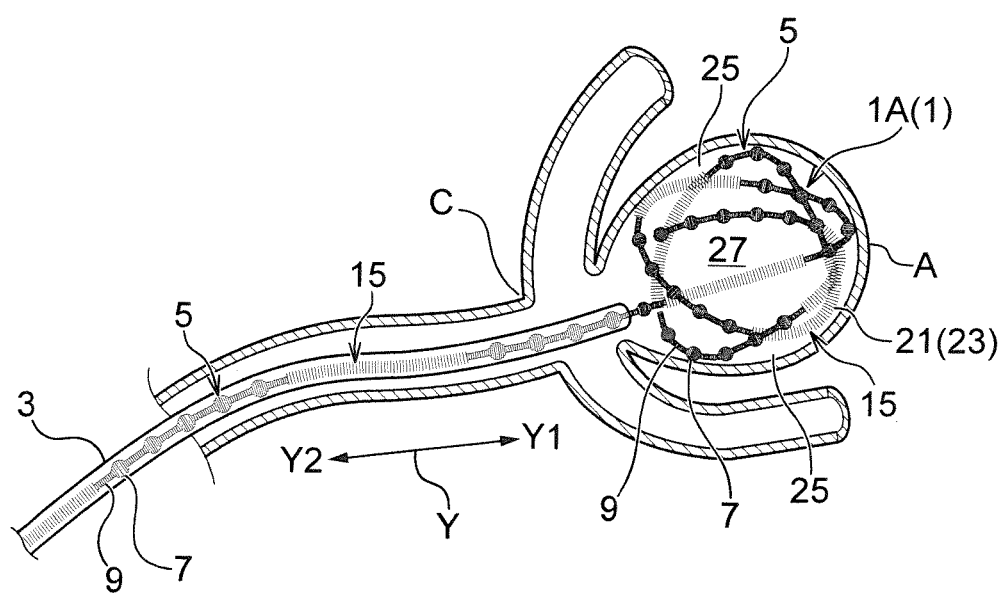
FIG. 5 is a view showing a first embodiment of the present invention and is an explanatory diagram explaining the formation of the frame.

(3) Step of Guiding the Embolic Coil (See FIG. 4 to FIG. 5)

Next, the process of guiding the embolic coil 1A into the aneurysm A using the embolic coil 1A according to the present embodiment is described in two stages: (A) immediately before the start of coil guiding, and (B) frame formation.

(A) Immediately Before the Start of Coil Guiding (See FIG. 4)

When guiding the embolic coil 1A, as described above in the aforementioned (1) Outline of catheter treatment that utilizes an embolic coil, as a preparation work, the catheter 3 is placed in the human body H and the distal end of the catheter 3 is guided to reach the inside of the aneurysm A. Next, the distal end Y1 of the embolic coil 1A in the longitudinal direction Y is inserted into the catheter 3 placed in the human body H from outside, and the embolic coil 1A is moved toward the aneurysm A along the inner wall surface of the catheter 3.

At this time, the embolic coil 1A can be inserted smoothly into the catheter 3, since in the embolic coil 1A according to the present embodiment, the large diameter coil portion 7 of the first coil portion 5 to be inserted first is formed by the spherical convex curved surface 17. In addition, the rectilinearity of the embolic coil 1A in the catheter 3 can be maintained, since the outer diameter of the large-diameter coil portion 7 of the first coil portion 5 of the embolic coil 1A and the outer diameter of the second coil portion 15 according to the present embodiment are the same, so that the outer peripheries thereof function as a guide. The above described arrangement therefore allows moving the embolic coil 1A smoothly. The distal end Y1 of the embolic coil 1A is then protruded from the distal end opening of the catheter 3 and brought into the aforementioned aneurysm A, and thereby the preparatory work prior to the guiding of the embolic coil 1A is completed.

(B) Frame Formation (See FIG. 5)

After completion of the preparatory work, the operation of guiding the embolic coil 1A is performed to advance the embolic coil 1A into the catheter 3. The embolic coil 1A delivered from the distal end opening of the catheter 3 is guided deeper into the aneurysm A, and the distal end Y1 of the embolic coil 1A first contacts the inner wall surface on the deeper side of the aneurysm A, and bends along the inner wall surface, and then goes out toward the front or the side.

The distal end portion of the embolic coil 1A is then fed out toward the front or the side and brought into contact with the inner surface of the aneurysm A of the relevant portion and is further folded back while being bent to form a ring-shaped portion 21.

Further, as the guiding of the embolic coil 1A progresses, a plurality of ring-shaped portions 21 are formed as shown in FIG. 5. These ring-shaped portions 21 form the frame 23, which serves as an outer shell member during guiding of the subsequent embolic coil 1A. Here, it is preferable that the amount of the first coil portion 5 and the second coil portion 15 in the plurality of ring-shaped portions 21 forming the frame 23 is appropriately set and used to match the size and shape of the aneurysm.

As described above, in the embolic coil 1A according to the present embodiment, when the embolic coil 1A is guided into the aneurysm A and when several ring-shaped portions 21, in a state curved into a ring shape in the aneurysm A, are produced to form the frame 23, even if the quantity of the ring-shaped portions 21 increases along with the progress of the formation of the frame 23 due to the presence of the flat cylindrical structure (second coil portion 15) portion, the possibility of catching is reduced. Therefore, in the embolic coil 1A according to the present embodiment, when forming the frame 23 in the aneurysm A, the frame 23 can be smoothly formed without catching.

Further, in the frame 23, at the stage when the frame 23 is formed, at a contact position (intersecting position) between the ring-shaped portions 21, a spot where the large-diameter coil portion 7 is caught is created due to the presence of the convex-concave structure (first coil portion 5). As a result, an anchor effect due to catching of the large-diameter coil portion 7 is produced, and the structure of the frame 23, that is, the three-dimensional structure by the plurality of ring-shaped portions 21 is therefore stabilized.

<In relation to Expansion and Deformation of Aneurysm Volume>

As the introduction of the embolic coil 1A progresses while the large diameter coil portion 7 is being caught, the volume of the aneurysm A expands and deforms more as the introduction of the embolic coil 1A progresses than at the beginning of introduction. In the present embodiment, since the flat cylindrical structure (second coil portion 15) portion is present at a constituent portion of the structure of the frame 23, when the volume of the aneurysm expands and deforms, the position where the large diameter coil portion 7 is caught can be moved along the cylindrical structure portion.

Here, the cylindrical structure (second coil portion 15) portion of the embolic coil 1A has a larger repulsive force to the curve and deformation than the convex-concave structure (first coil portion 5) portion. Due to the repulsive force of the cylindrical structure portion, the force for expanding the frame 23 outward is stronger than conventional embolic coils which only have a convex-concave structure. This repulsive force moves the position where the large diameter coil portion 7 becomes caught, in a direction that expands the frame 23 along the cylindrical structure portion. In other words, the frame 23 can become larger to match the expansion and deformation of the volume of the aneurysm A. Thereby, it is possible to reduce the possibility that the position of the frame 23 becomes unstable in the expanded and deformed aneurysm A. The ring-shaped portion 21 is positioned along the inner surface of the enlarged and deformed aneurysm A, and the frame 23 can be held firmly in the aneurysm A.

Further, in the present embodiment, the cylindrical structure portion is repeatedly present in the constituent portion of the structure of the frame 23. It is a state in which portions, which have a large repulsive force to the curve and deformation, repeatedly exist in the constituent portion of the structure of the frame 23. The frame 23 can in this way become larger even more effectively following the expansion and deformation of the volume of the aneurysm A.

In this embodiment, since the secondary shape for forming the frame is further formed at the distal end portion of the embolic coil 1A, an elastic force for returning to the secondary shape acts so that the ring-shaped portion 21 is more smoothly formed.

Even if the secondary shape is not formed, the embolic coil 1A itself receives a curving force along the inner surface of the aneurysm A within the aneurysm A, and an outward expanding force is generated by the repulsive force of the embolic coil that received the curving force. Due to this force, the ring shaped portion 21 is positioned and held along the inner surface of the aneurysm A. In other words, the ring-shaped portion 23 is easily formed even if no secondary shape is formed.

Figure 6:
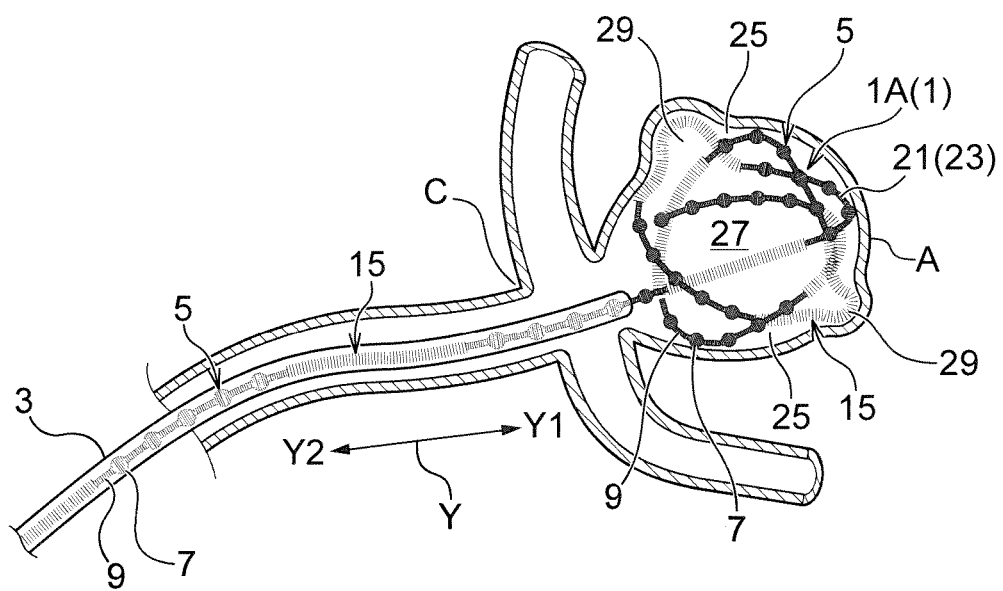
FIG. 6 is a view showing a first embodiment of the present invention, and is an explanatory diagram explaining formation of the frame in an irregularly shaped aneurysm.

(4) When Filling an Embolic Coil into an Irregularly Shaped Aneurysm (See FIG. 6)

Next, descriptions will be made on the process of guiding the embolic coil 1A, in the case where a void region 29 is formed between the outer surface of the frame 23 formed in the aneurysm A and the inner surface of the aneurysm because of the irregularly shaped aneurysm A as shown in FIG. 6.

If the aneurysm A is irregularly shaped, the void region 29 as shown may be formed between the outer surface of the frame 23 formed by the ring-shaped portion 21 and the inner surface of the aneurysm A.

In this embodiment, even in such a case, since the cylindrical structure (second coil portion 15) portion allows smooth guidance with minimal catching, the cylindrical structure (second coil portion 15) portion can reach the void region 29 through a clearance 25 of the ring-shaped portion 21 of the frame 23 during its formation process.

As described above, the cylindrical structure (second coil portion 15) portion can smoothly spread to the void region 29 and an inner space 27 of the frame 23 through the clearance 25 of the ring-shaped portion 21. The cylindrical structure (second coil portion 15) is therefore guided not only into the inner space 27 of the frame 23 but also into the void region 29 so as to fill both the inner space 27 and the void region 29.

According to the present embodiment, when the frame 23 is formed, due to the presence of the cylindrical structure (second coil portion 15), the cylindrical structure (second coil portion 15) can protrude from the inside of the frame 23 to the outside with little resistance, through the clearance 25 of the ring-shaped portion 21 forming the frame 23. Therefore, even in the case where the shape of the aneurysm A is irregular and the void region 29 is likely to form between the outer side of the frame 23 and the inner surface of the aneurysm A, the cylindrical structure (second coil portion 15) can easily enter to the void region 29 by protruding outwards from the frame 23. The frame 23 can therefore be formed not only for a regularly shaped aneurysm but also for an irregularly shaped aneurysm.

Second Embodiment (See FIG. 7 to FIG. 12)

Figure 7:
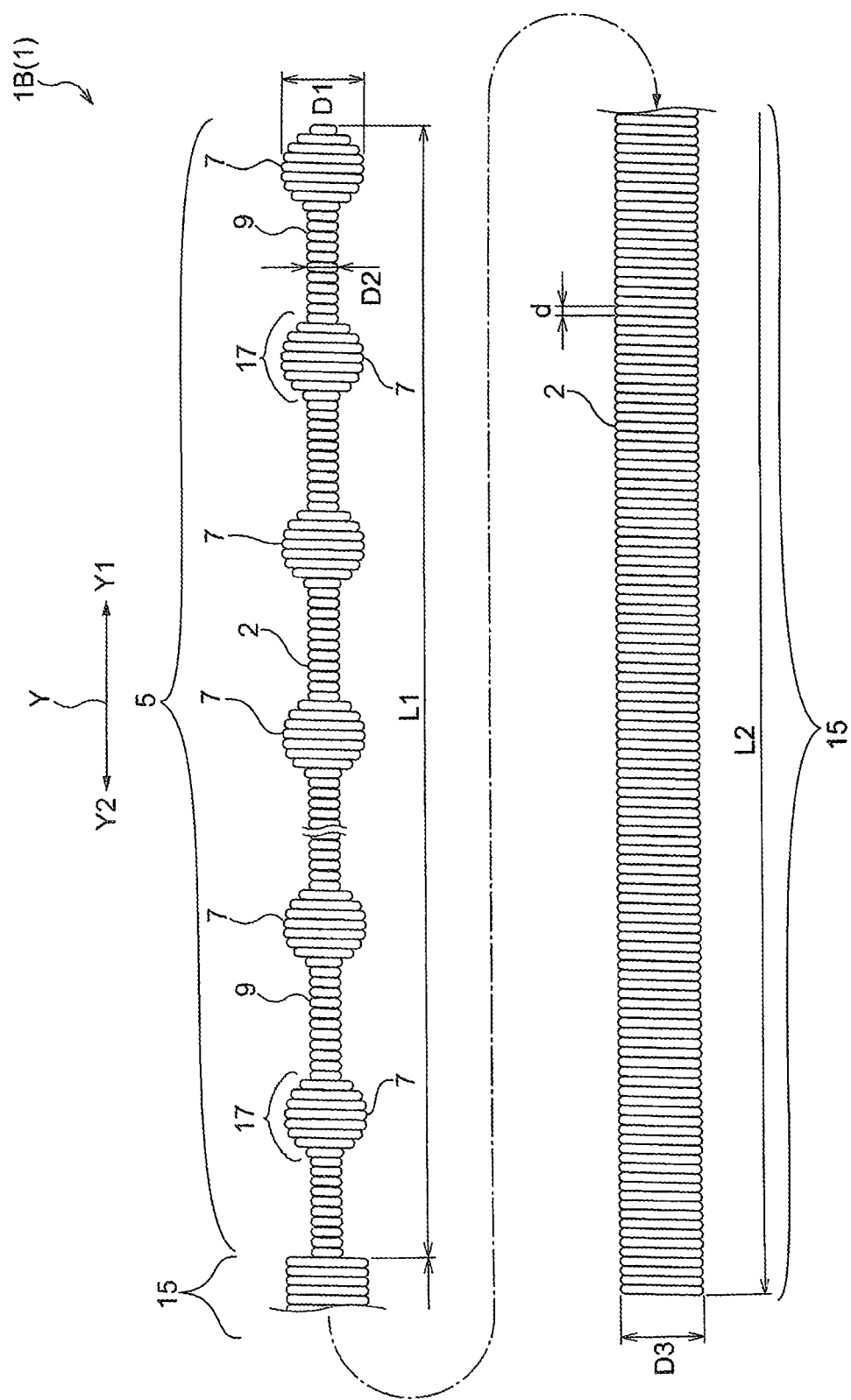
FIG. 7 is a view showing a second embodiment of the present invention, and is a side view showing a primary shape of an embolic coil.
Figure 8:
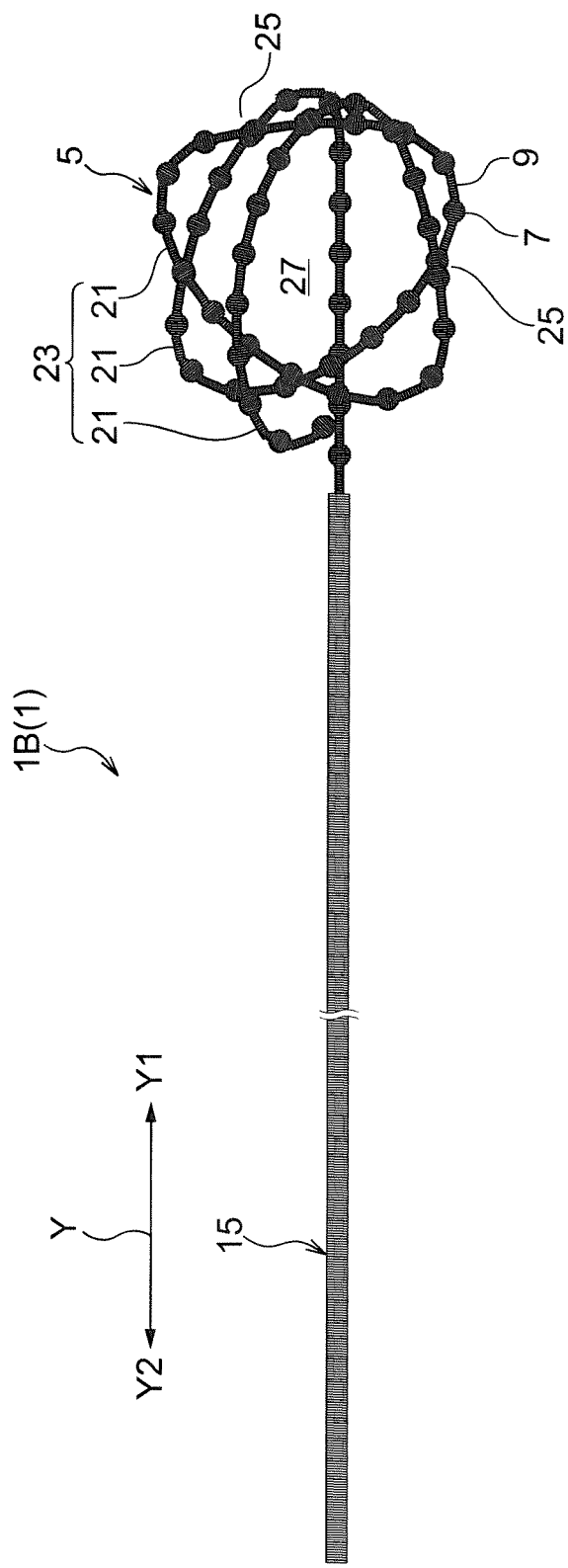
FIG. 8 is a view showing a second embodiment of the present invention, and is a side view showing a secondary shape of an embolic coil.

(1) Specific Configuration of the Embolic Coil (See FIG. 7 and FIG. 8)

An embolic coil 1B according to the second embodiment differs from the embolic coil 1A of the first embodiment in that instead of a repeating structure of the first coil portion 5 and the second coil portion 15 of the embolic coil 1A, the first coil portion 5 is located in the distal end of the embolic coil 1B and all the remaining portions of the embolic coil 1B connected to the first coil portion 5 are constituted by the second coil portion 15.

In the embolic coil 1B according to the present embodiment, a single first coil portion 5 with a predetermined length L1 is arranged on the Y1 side distal end of the embolic coil 1B in the longitudinal direction Y, and one second coil portion 15 with a predetermined length L2 is likewise arranged at a portion from a terminal end of the first coil portion 5 to a terminal end Y2 of the embolic coil 1B in the longitudinal direction Y.

Preferably, the "predetermined length L1" in "the first coil portion 5 with a predetermined length L1" is set in consideration of a length assumed as the portion constituting the frame 23 described later. Preferably, the second coil portion 15 is also partly included in the portion constituting the frame 23.

FIG. 7 shows the embolic coil 1B in the primary shape during movement inside the catheter 3. However, as shown in FIG. 8, the embolic coil 1B of a secondary shape having a larger coil diameter (for example, 3 mm to 30 mm) may be formed in advance so that the frame 23 is more easily formed to match the size and shape of the aneurysm A. The formation of the secondary shape may be omitted in the same way as the first embodiment.

Since the specific configurations of the first coil portion 5 and the second coil portion 15 of the embolic coil 1B are the same as the embolic coil 1A according to the above-described first embodiment, a detailed description thereof is omitted.

Figure 9:
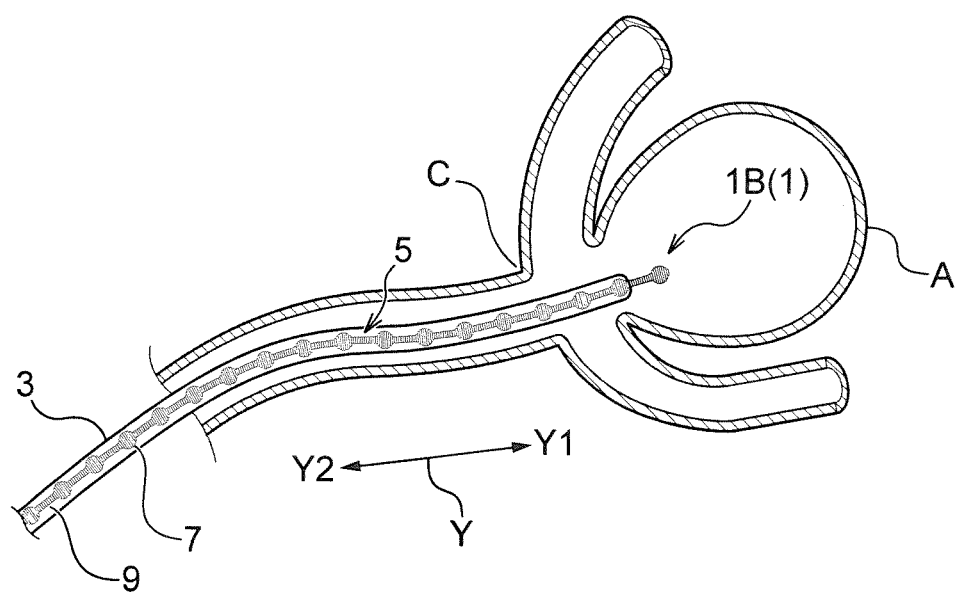
FIG. 9 is a view showing a second embodiment of the present invention, and is an explanatory diagram showing an embolic coil before starting to guide.
Figure 10:
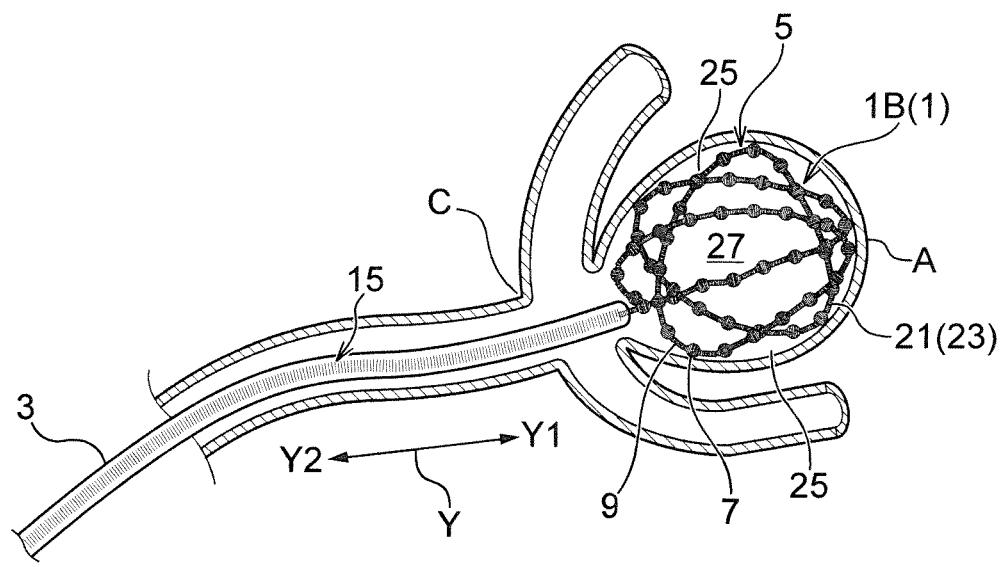
FIG. 10 is a view showing a second embodiment of the present invention, and is an explanatory diagram explaining formation of the frame.
Figure 11:
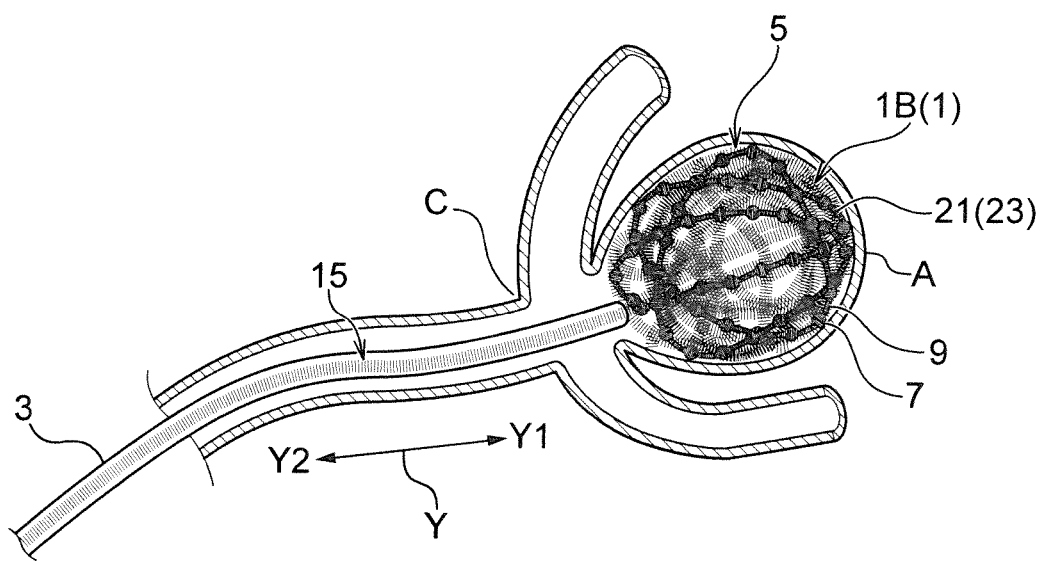
FIG. 11 is a view showing a second embodiment of the present invention, and is an explanatory diagram showing a state in which guiding of an embolic coil has proceeded further from formation of the frame.

(2) Step for Guiding the Embolic Coil (See FIG. 9 to FIG. 11)

A process for guiding the embolic coil 1B into the aneurysm A using the embolic coil 1B according to the present embodiment is next described while grouped into the following three stages: (A) immediately before the start of guiding, (B) start of frame formation, (C) a state in which guiding the embolic coil proceeds even further after frame formation.

(A) Immediately Before the Start of Guiding (See FIG. 9)

The distal end Y1 of the embolic coil 1B in the longitudinal direction Y is inserted into the catheter 3 from the outside, and the embolic coil 1B is moved toward the aneurysm A along the inner wall surface of the catheter 3.

At this time, in the embolic coil 1B according to the present embodiment, the first coil portion 5 is positioned at the distal end, and the remaining part of the embolic coil 1B connected to the first coil portion 5 is constituted by the second coil portion 15. The outer periphery of the second coil portion 15 effectively serves as a guide when advancing in the catheter 3, and the rectilinearity of the embolic coil 1B in the catheter 3 can be even further enhanced.

(B) Frame Formation (See FIG. 10)

The embolic coil 1B fed from the distal end opening of the catheter 3 is guided deeper into the aneurysm A, and the distal end Y1 of the embolic coil 1B first contacts the inner wall surface on the deeper side of the aneurysm A, and bends along the inner wall surface, and then goes out toward the front or the side.

The distal end portion of the embolic coil 1B fed out toward the front or the side is then brought into contact with the inner surface of the aneurysm A at the relevant portion and is further folded back while being bent to form a ring-shaped portion 21.

Further, as guiding of the embolic coil 1B progresses, as shown in FIG. 10, a plurality of ring-shaped portions 21 are formed. The frame 23 functions as an outer shell member by way of these ring-shaped portions 21 during guiding of the follow-up embolic coil 1B. As shown in FIG. 10, the present embodiment differs from the first embodiment in that the frame 23 is initially formed only with the convex-concave structure (first coil portion 5). However, in the stage shown in FIG. 10, the amount of the ring-shaped portion 21 in the aneurysm A is small so there is little possibility that the guiding operation will be obstructed by catching of the large-diameter coil portion 7.

Furthermore, in this embodiment, since the secondary shape shown in FIG. 8 is formed at the first coil portion 5 of the embolic coil 1B, an elastic force for returning to the secondary shape acts so that the ring-shaped portion 21 is more smoothly formed.

Even if the secondary shape is not formed, the embolic coil 1B itself receives a curving force along the inner surface of the aneurysm A within the aneurysm A, and a force for expanding outward is generated by the repulsive force of the embolic coil that received the curving force. Due to this force, the ring shaped portion 21 is positioned and held along the inner surface of the aneurysm A. The ring-shaped portion is in this way easily formed even if no secondary shape is formed.

Then, at the intersecting position between ring-shaped portions 21 forming the frame 23, a locking effect (anchor effect) is exerted by the convex-concave structure of the first coil portion 5, so that the frame 23 is smoothly formed in a stable state with no possibility of becoming unhooked.

(C) Guiding of the Second Coil Portion (See FIG. 11)

When guiding of the first coil portion 5 is complete, the guiding of the subsequent second coil portion 15 starts. Since the outer diameter D3 of the second coil portion 15 has a uniform cylindrical shape with little convexity and concavity, smooth guidance is performed with minimal catching. As shown in FIG. 11, the clearance 25 of the ring-shaped portion 21 of the frame 23 and the inner space 27 of the frame 23 are densely filled to complete the frame 23.

After completion of the frame 23, the subsequent second coil portion 15 encounters little resistance and can push open a small clearance via the portion of the previously guided embolic coil 1B to enter every corner in the aneurysm A. The filling ratio can thereby be improved.

In the second embodiment, when a required amount of the embolic coil 1B is guided and filled into the aneurysm A, an appropriate position on the second coil portion 15 of the embolic coil 1B is cut by using an appropriate separating mechanism etc. (not shown). After cutting, the remaining embolic coil 1B, which was not used for filling, and the catheter 3 are pulled out and removed from the human body H.

In the aneurysm A filled with the embolic coil 1B, an inflow of blood flowing in the blood vessel is suppressed by the presence of the embolic coil 1B, and a thrombus is positively formed and solidified in the aneurysm A, so that rupture of the aneurysm A is suppressed.

Incidentally, the above cutting process can of course be rendered unnecessary by preparing in advance a length of the embolic coil 1B sufficient for forming the frame 23, and after the frame 23 is formed, guiding another embolic coil which is separate from the embolic coil 1B into the frame 23 so as to have a length necessary for forming the frame 23.

As described above, according to the embolic coil 1B of the present embodiment, when the embolic coil 1B is guided into the aneurysm A and several ring-shaped portions 21, in a state of being curved in a ring shape in the aneurysm A are produced to form the frame 23, the possibility of the large-diameter coil portion 7 catching is reduced because of the presence of the flat cylindrical structure (second coil portion 15) portion. Therefore, according to the embolic coil 1B of the present embodiment, when forming the frame 23 in the aneurysm A, the formation of the frame 23 can be smoothly performed without catching.

Further, in the frame 23, at the stage where the frame 23 is formed, at a contact position (intersecting position) between the ring-shaped portions 21, a place where the large-diameter coil portion 7 is caught is created because of the presence of the convex-concave structure (first coil portion 5). As a result, an anchor effect due to catching of the large-diameter coil portion 7 is produced, and thereby the structure of the frame 23 or namely the three-dimensional structure due to the plurality of ring-shaped portions 21 is stabilized.

<Expansion and Deformation of the Aneurysm Volume>

Since the guiding of the embolic coil 1A progresses further while the large diameter coil portion 7 is caught, the volume of the aneurysm A expands and deforms more as the guiding of the embolic coil 1A progresses than at the beginning of guiding. According to the present embodiment, since the flat cylindrical structure (second coil portion 15) portion is in the portion forming the structure of the frame 23, when the volume of the aneurysm is expanded and deformed, the position where the large diameter coil portion 7 is caught can be moved along the cylindrical structure portion.

Due to a large repulsive force of the cylindrical structure (second coil portion 15) portion in the embolic coil 1B, the force for expanding the frame 23 outward is stronger than conventional embolic coils which only have the convex-concave structure. Due to this repulsive force, the position where the large diameter coil portion 7 is caught is moved in a direction for expanding the frame 23 along the cylindrical structure portion. In other words, the frame 23 can grow larger to follow up on the expansion and deformation of the volume of the aneurysm A. Therefore, the concern that the position of the frame 23 will become unstable in the expanded and deformed aneurysm A can in this way be reduced. The ring-shaped portion 21 is positioned along the inner surface of the enlarged and deformed aneurysm A, and the frame 23 can be held firmly in the aneurysm A.

Figure 12:
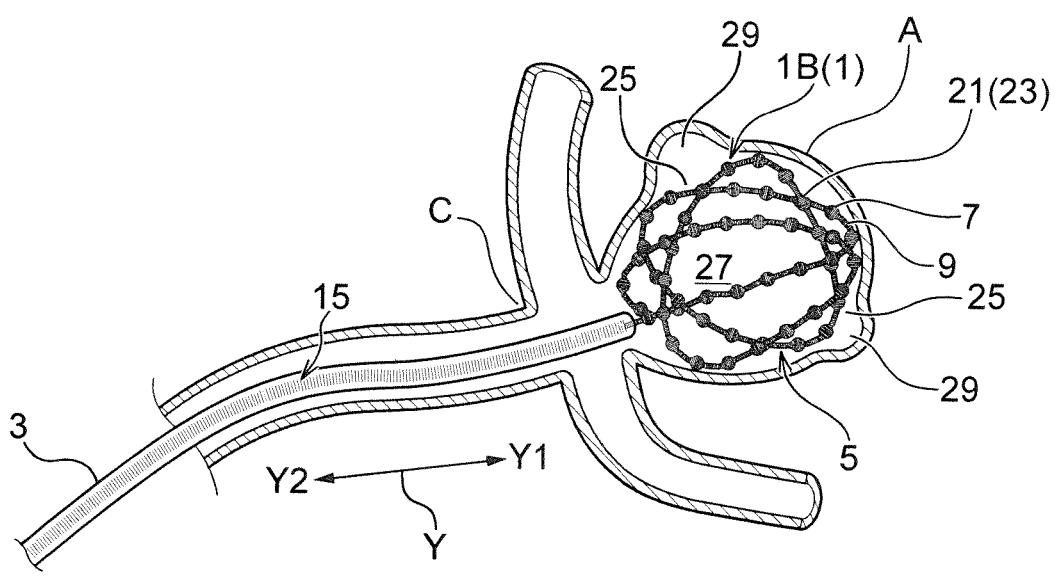
FIG. 12 is a view showing a second embodiment of the present invention, and is an explanatory diagram explaining frame formation in an irregularly shaped aneurysm.
Figure 13:
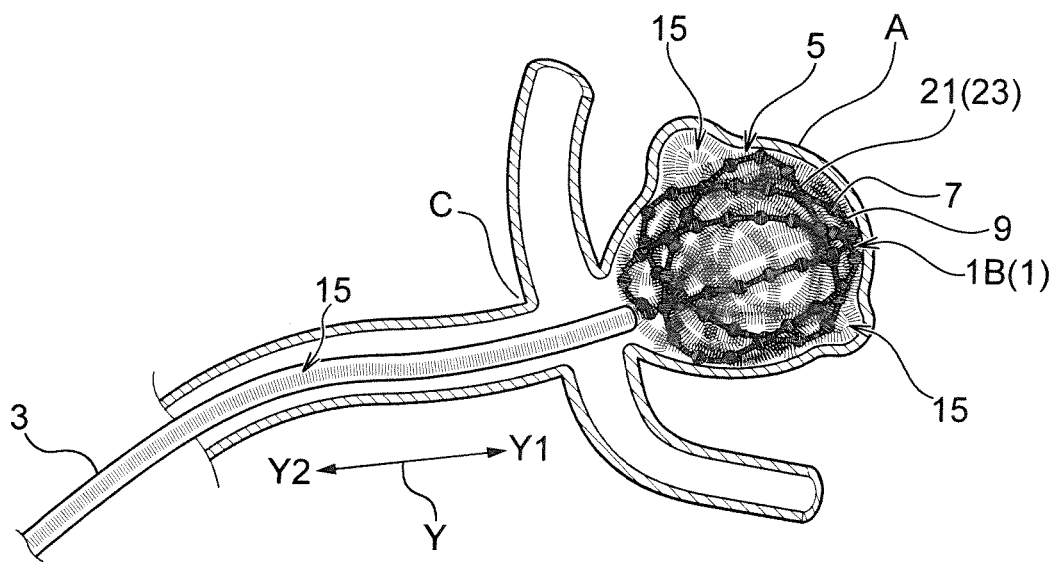
FIG. 13 is a view showing a second embodiment of the present invention, and is an explanatory diagram showing a state in which guiding of an embolic coil has proceeded further from forming the frame in an irregularly shaped aneurysm.

(3) When Filling an Embolic Coil into an Irregularly Shaped Aneurysm (See FIG. 12 and FIG. 13)

Next, the process for guiding the embolic coil portion 1B will be described for the case as shown in FIG. 12 when the void region 29 is formed between the outer surface of the frame 23 formed in the aneurysm A and the inner surface of the aneurysm A since the aneurysm A is irregular.

In this embodiment, since the cylindrical structure (second coil portion 15) portion allows smooth guidance with minimal catching, the cylindrical structure (second coil portion 15) portion can reach the void region 29 through the clearance 25 of the ring-shaped portion 21 of the frame 23 during its formation process (FIG. 13).

As described above, the cylindrical structure (second coil portion 15) portion can smoothly spread to the void region 29 and an inner space 27 of the frame 23 by way of the clearance 25 of the ring-shaped portion 21. The cylindrical structure (second coil portion 15) is in this way guided not only into the inner space 27 of the frame 23 but also into the void region 29 to fill both of the inner space 27 and the void region 29.

According to the present embodiment, when the frame 23 is formed, due to the presence of the cylindrical structure (second coil portion 15), the cylindrical structure (second coil portion 15) portion can protrude outwards from the inside of the frame 23 to the outside with little resistance, through the clearance 25 of the ring-shaped portion 21 forming the frame 23. Therefore, even in the case where the shape of the aneurysm A is irregular and the void region 29 is likely to form between the outer side of the frame 23 and the inner surface of the aneurysm A, the cylindrical structure (second coil portion 15) can easily enter to the void region 29 by sticking out from the frame 23. Therefore, the frame 23 can easily be formed not only for regularly shaped aneurysms but also for irregularly shaped aneurysms.

Figure 14:
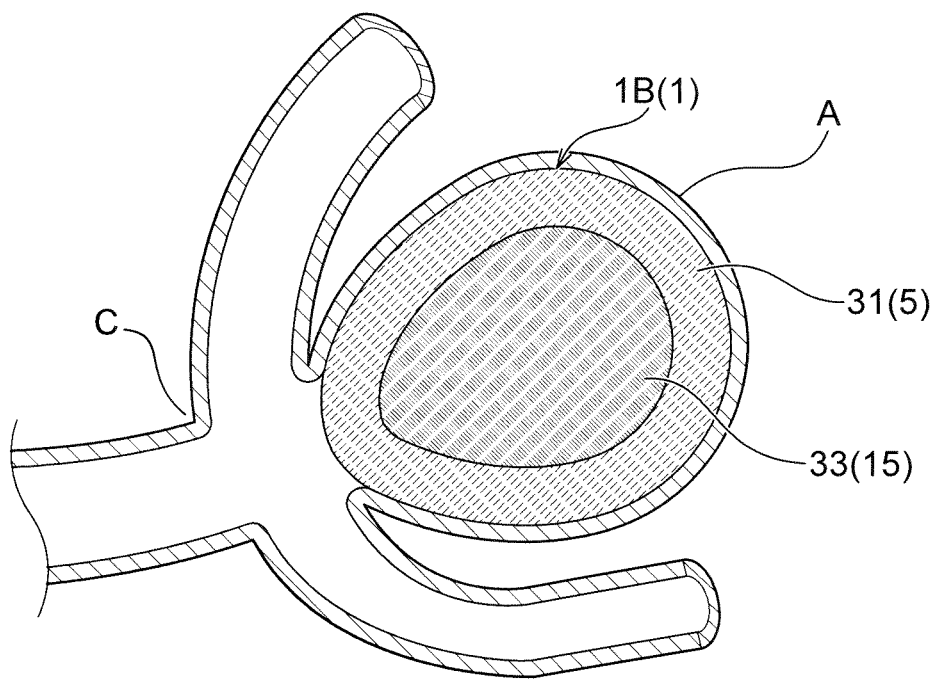
FIG. 14 is a view showing a second embodiment of the present invention, and is a schematic view showing an example of the filling state of the embolic coil after completion of filling.

FIG. 14 is a simplified schematic view showing a filled state of an aneurysm, in which the embolic coil 1B according to the present embodiment was filled into the aneurysm as shown in FIG. 10, and the subsequent second coil portion 15 was guided, and then filling was completed.

A primary filled layer 31, which is mainly formed by the first coil portion 5 by filling this first coil portion 5, is formed in an outer region near the inner surface of the aneurysm A. And a secondary filled layer 33, which is formed by filling the second coil portion 15, is formed in a region inside the primary filled layer.

Incidentally, FIG. 14 is a simplified illustration allowing an easier understanding of the state in which the embolic coil 1B is filled into the aneurysm A. Usually, the primary filled layer 31 and the secondary filled layer 33 are seldom divided into such a simple layer arrangement. Since the guidance of the embolic coil 1B advances further to the clearance portion in the state shown in FIG. 10, a region where the embolic coil 1B is present as well as the boundary between the two layers 31, 33 are complex. In other words, FIG. 14 explains that the primary filled layer 31 and the secondary filled layer 33 generally tend to be formed in layer shapes.

In this way, when the secondary filled layer 33 located on the inner side is constituted by filling the cylindrical structure (second coil portion 15), a strong repulsive force against the curve and deformation of the cylindrical structure (of the second coil portion 15) is obtained. The frame 23 can therefore more effectively follow up on the expansion and deformation of the aneurysm volume and become larger.

Figure 15:
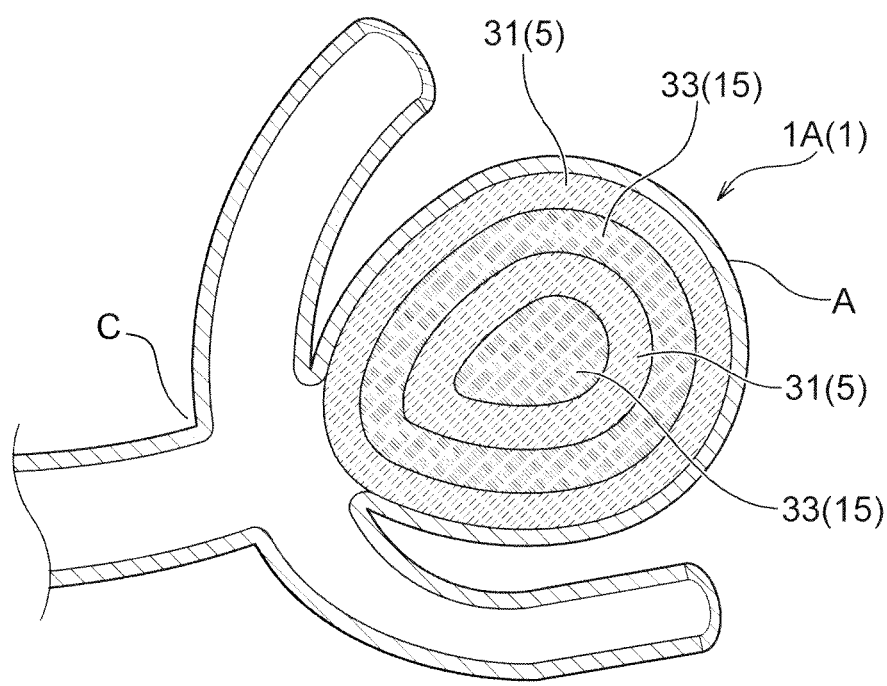
FIG. 15 is a view showing a first embodiment of the present invention, and is a schematic view showing an example of the embolic coil filling state after completion of filling.

FIG. 15 is a view schematically showing a filled state of the aneurysm, in which guiding of the embolic coil 1A with a repeating structure starts, the guiding continues, and filling is completed. Here, a length of the first coil portion 5 in the embolic coil 1A according to the first embodiment is made long enough to form the frame 23 just by the first coil portion 5, and a length of the second coil portion 15 is made about the same as the first coil portion 5.

The primary filled layer 31 is mainly formed in the region on the outer side near the inner surface of the aneurysm A, and the secondary filled layer 33 is mainly formed in the region inside the primary filled layer 31. Here, the amount of the primary filled layer 31 corresponds to the length of the first coil portion 5 located in a distal end formed by filling the first coil portion of the distal end, and the secondary filled layer 33 is formed by filling the second coil portion 15 that is subsequent to the first coil portion 5 located in the distal end. Next, the primary filled layer 31 with the amount corresponding to the length of the first coil portion 5 in the second order is mainly formed. And the secondary filled layer 33, which is formed by filling the second coil portion 15 in the second order following the first coil portion 5, is mainly formed in the region inside the primary filled layer 31.

Incidentally, FIG. 15 is a simplified illustration to allow an easier understanding of the state in which the embolic coil 1A is filled into the aneurysm A. Under actual circumstances, the primary filled layer 31 and the secondary filled layer 33 are seldom divided into such a simple layer structure. The region where the embolic coil 1A is present as well as the boundary between the two layers 31, 33 are complex. In other words, FIG. 15 explains that the primary filled layer 31 and the secondary filled layer 33 generally tend to be formed in layer shapes.

In this way, a filled state of the embolic coil 1B having a multiple layer structure in which the primary filled layer 31 and the secondary filled layer 33 generally tend to repeat is formed within the aneurysm A. The filled state of the embolic coil 1B, which is more stable and which has a higher filling ratio can thus be obtained.

Figure 16:
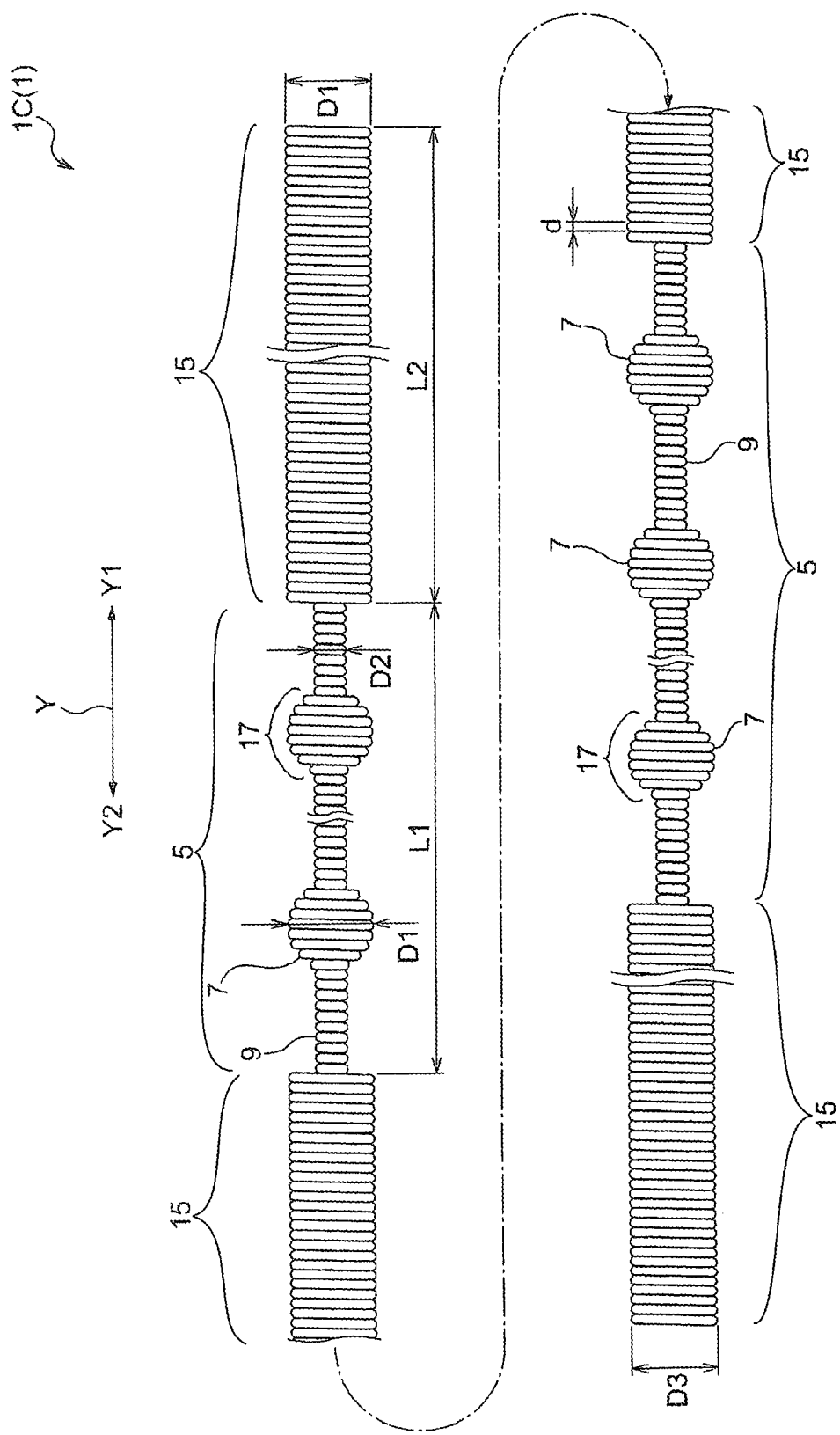
FIG. 16 is a view showing a third embodiment of the present invention, and is a side view showing a primary shape of an embolic coil.

Third Embodiment (See FIG. 16)

In the embolic coil 1C according to the third embodiment, the order of the first coil portion 5 and the second coil portion 15 according to the above-described first embodiment is reversed so that the second coil portion 15 on the distal end Y1 side of the embolic coil 1C in the longitudinal direction Y, and the first coil portion 5 are arranged behind the second coil portion 15, and thereafter the second coil portion 15 and the first coil portion 5 are repeatedly arranged in this order toward the terminal end Y2 of the embolic coil 1C in the longitudinal direction.

Since the specific configurations of the first coil portion 5 and the second coil portion 15 of the embolic coil 1C are the same as the configuration of the embolic coil 1A according to the first embodiment and the embolic coil 1B according to the second embodiment, described above, a detailed description thereof is omitted.

According to the present embodiment, the catching by itself like the first coil portion 5 cannot be expected because the furthest distal end is the second coil portion 15, however, the substantially same effect can be obtained in other respects.

Figure 17:
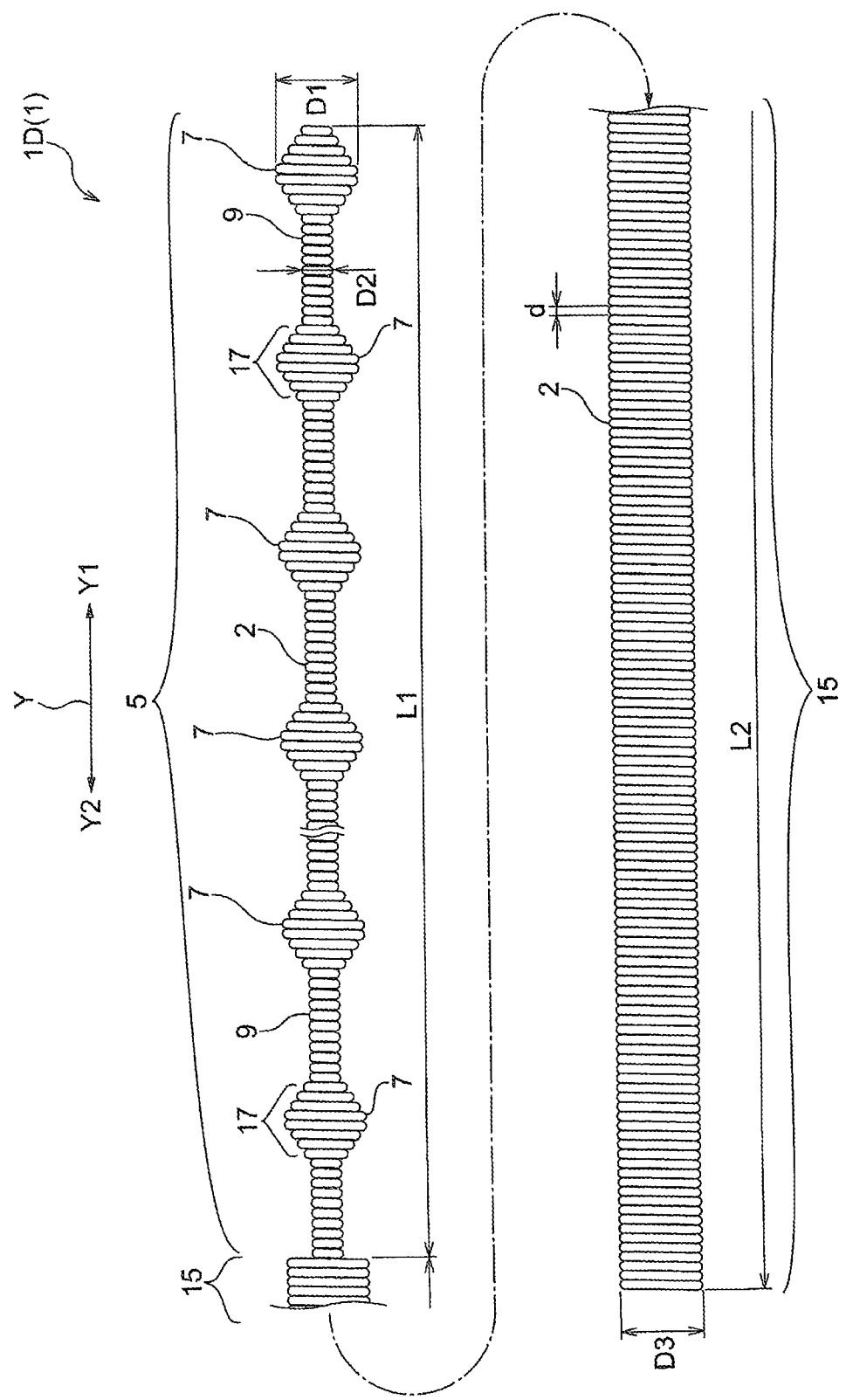
FIG. 17 is a view showing a fourth embodiment of the present invention, and is a side view showing a primary shape of an embolic coil.

Fourth Embodiment (See FIG. 17)

The embolic coil 1D according to the fourth embodiment is different from the embolic coil 1B according to the second embodiment in that the shape of the spherical large-diameter coil portion 7 in the first coil portion 5 of the embolic coil 1B according to the second embodiment is a convex shape like the bead of an abacus in which the bottom surfaces of two triangular pyramids are joined together.

Since the specific configurations of the small-diameter coil portion 9 of the first coil portion 5 and the second coil portion 15, in the embolic coil 1C, are the same as the configuration of the embolic coil 1A according to the first embodiment and the embolic coil 1B according to the second embodiment described above, a detailed description thereof is omitted.

With the embolic coil 1D according to the present embodiment configured in this way, the same functions and effects as those of the embolic coil 1B according to the second embodiment are exhibited.

Figure 18:
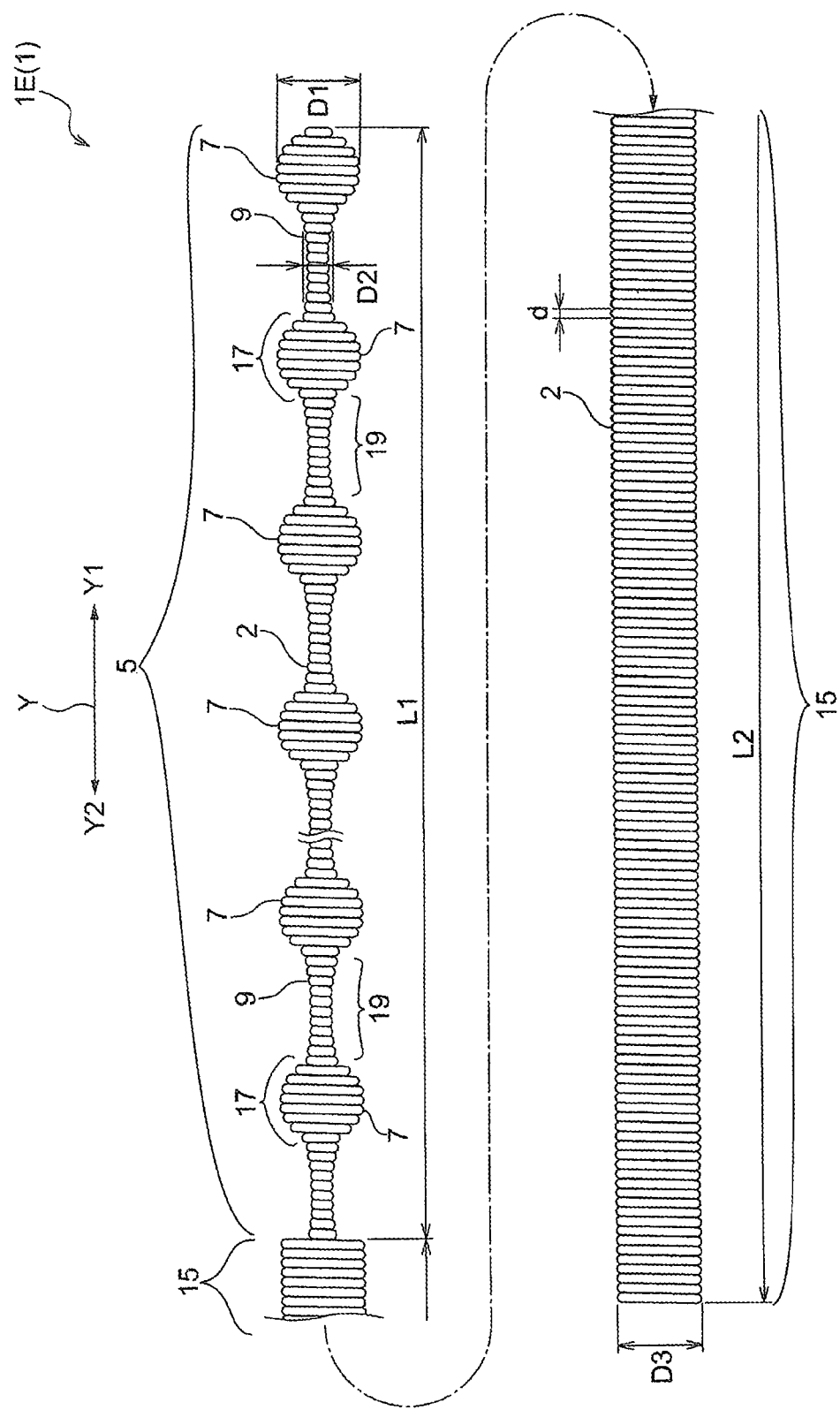
FIG. 18 is a view showing a fifth embodiment of the present invention, and is a side view showing a primary shape of an embolic coil.

Fifth Embodiment (See FIG. 18)

In the embolic coil 1E according to the fifth embodiment, the shape of the small diameter coil portion 15, which is uniformly in a cylindrical shape in the longitudinal direction Y of the first coil portion 5 of the embolic coil 1B according to the second embodiment described above, is changed, and the concave curved surfaces 19 in the spherical shape are formed on the outer surface of the small-diameter coil portion 15.

Since the specific configurations of the large-diameter coil portion 7 of the first coil portion 5 and the specific configurations of the second coil portion 15, in the embolic coil 1E, are the same as those of the embolic coil 1B according to the second embodiment described above, a detailed description thereof is omitted.

The embolic coil 1E according to the present embodiment configured in this way also exhibits the same functions and effects as the embolic coil 1B according to the second embodiment described above. Further, compared to the cylindrical small diameter portion 9 wound with the uniform diameter adopted in the second embodiment; in this embodiment, due to the spherical concave curved surface 19 formed on the outer surface of the coil portion 9, the sliding resistance of the embolic coil 1E is reduced to allow smooth guiding of the embolic coil 1E with little possibility of the large diameter coil portion 7 catching. Easier bending is also achieved compared to the embodiment having a uniform diameter D2.

Other Embodiments

The embolic coil 1 according to the present invention is generally based on the configuration as described above, but of course changing or omitting a portion of the configuration within a scope not deviating from the essentials of the present invention is permissible.

For example, the lengths of the large-diameter coil portion 7 and the small-diameter coil portion 9, which are alternately arranged, can be appropriately adjusted depending on the wire diameter d of the wire 2, and the size and shape of the aneurysm A, etc.

Further, the shape of the large diameter coil portion 7 is not limited to the spherical shape and the abacus bead shape described in the above embodiments, but may be formed in other shapes such as a streamline shape or a cylindrical shape.

Further, in the above-described repetitive structure, the length L1 of the first coil portion 5 and the length L2 of the second coil portion 15 are described such that the same L1 and the same L2 are repeated. However, all of the L1 need not be the same, and all of the L2 need not be the same and may be different.

In addition, the concave curved surface 19 in the fifth embodiment is provided over the entire length of the small-diameter coil portion 9. However, the concave surface 19 may be partially provided such as at a boundary portion with the large-diameter coil portion 7. Also, the concave curved surface 19 is not limited to a spherical shape in the same way as the convex curved surface 17 applied to the large diameter coil portion 7, but may be formed into various types of concave curved surfaces.

In addition, the secondary shape formed at the distal end portion of the embolic coil portion may be omitted and an embolic coil may be formed in just a primary shape.

The secondary shape may be formed only in the first coil portion 5 of the distal end portion, or only in the second coil portion 15 of the distal end portion. Or, the secondary shape may be formed in both of the coil portions 5 and 15.

The invention claimed is:

1. An embolic coil formed by being spirally wound by an element wire to be filled into an aneurysm, comprising:
a first coil portion that contains at least three large-diameter coil portions wound to have a large diameter and at least three small-diameter coil portions wound to have a diameter smaller than that of the large-diameter coil portions, said the large-diameter coil portions and the small-diameter coil portions being alternately present in a longitudinal direction of the embolic coil; and
a second coil portion, which is continuous with the first coil portion and wound to have a flatter surface than the first coil portion, wherein
the second coil portion is at least three times longer than the large-diameter coil portions of the first coil portion in the longitudinal direction,
each of the large-diameter coil portions has a maximum outer diameter in a center and an outer diameter of each of the large-diameter coil portions decreases gradually and symmetrically in the longitudinal direction, and
the first coil portion contains the small-diameter coil portions between the adjacent large-diameter portions that are directly connected thereto.

2. The embolic coil according to claim 1, characterized in that
an outer diameter of the second coil portion is the same as a maximum outer diameter of each of the large-diameter coil portions.

3. The embolic coil according to claim 1, characterized in that
the first coil portion having a predetermined length is positioned at a distal end of the embolic coil.

4. The embolic coil according to claim 3, characterized in that
a portion of the distal end of the embolic coil continuing to the first coil portion is provided with the second coil portion having a length longer than the first coil portion.

5. The embolic coil according to claim 1, characterized in that
the first coil portion having a predetermined length and the second coil portion having a predetermined length are repeatedly provided in the longitudinal direction.

6. The embolic coil according to claim 1, characterized in that
each of the large-diameter coil portions is wound such that an outer surface forms a spherical convex curved surface.

7. The embolic coil according to claim 1, characterized in that
each of the small-diameter coil portions is wound such that an outer surface forms a spherical concave curved surface.

8. The embolic coil according to claim 1, characterized in that
a primary shape, in which the first coil portion and the second coil portion are formed, is formed relative to the wire, and a secondary shape used for forming a frame is formed relative to a predetermined length portion of a distal end of the embolic coil.

9. The embolic coil according to claim 1, wherein
a length of the second coil portion in the longitudinal direction is the same or longer than a length of the first coil portion.

* * * * *